United States Patent
Kim

(10) Patent No.: US 10,441,249 B2
(45) Date of Patent: Oct. 15, 2019

(54) ULTRASOUND DIAGNOSIS APPARATUS AND METHOD OF OPERATING THE SAME

(71) Applicant: SAMSUNG MEDISON CO., LTD., Hongcheon-gun, Gangwon-do (KR)

(72) Inventor: Han-eol Kim, Gangwon-do (KR)

(73) Assignee: Samsung Medison Co., Ltd., Hongcheon-gun, Gangwon-do (KR)

( * ) Notice: Subject to any disclaimer, the term of this patent is extended or adjusted under 35 U.S.C. 154(b) by 323 days.

(21) Appl. No.: 14/744,446

(22) Filed: Jun. 19, 2015

(65) Prior Publication Data
US 2016/0183925 A1    Jun. 30, 2016

(30) Foreign Application Priority Data

Dec. 31, 2014   (KR) .................. 10-2014-0195374

(51) Int. Cl.
*A61B 8/08*      (2006.01)
*G16H 40/63*    (2018.01)
(Continued)

(52) U.S. Cl.
CPC .............. *A61B 8/483* (2013.01); *A61B 8/463* (2013.01); *A61B 8/523* (2013.01); *A61B 8/5207* (2013.01);
(Continued)

(58) Field of Classification Search
CPC ........... A61B 8/00; A61B 8/483; A61B 8/463; A61B 8/523; A61B 8/5207; A61B 8/466;
(Continued)

(56) References Cited

U.S. PATENT DOCUMENTS

| 5,720,291 A | 2/1998 | Schwartz |
|---|---|---|
| 6,254,540 B1 | 7/2001 | Kikuchi et al. |

(Continued)

FOREIGN PATENT DOCUMENTS

| JP | 07184906 A | 7/1995 |
|---|---|---|
| JP | 10-234662 A | 9/1999 |

(Continued)

OTHER PUBLICATIONS

Extended European Search Report issued in European Application No. 15166202.0 dated Jun. 6, 2016.

*Primary Examiner* — Luther Behringer
*Assistant Examiner* — Sean D Mattson
(74) *Attorney, Agent, or Firm* — Morgan, Lewis & Bockius LLP

(57) ABSTRACT

An ultrasound diagnosis apparatus includes: an ultrasound probe; a display; an image processor; and a memory storing instructions that, when executed by the image processor, perform operations. The operations includes acquiring ultrasound data about an object; generating an ultrasound image, based on the acquired ultrasound data; generating a first marker for a first object of interest (OOI) which is not included in the generated ultrasound image; displaying the generated ultrasound image and a map image representing a viewing point corresponding to the ultrasound image, a viewing direction, a region that a virtual ray reaches, and a position of the first OOI; and marking the first marker to correspond to the position of the first OOI on the ultrasound image and the map image.

18 Claims, 9 Drawing Sheets

(51) Int. Cl.
*A61B 8/00* (2006.01)
*A61B 8/12* (2006.01)
*G01S 7/52* (2006.01)

(52) U.S. Cl.
CPC .............. *G16H 40/63* (2018.01); *A61B 8/085* (2013.01); *A61B 8/12* (2013.01); *A61B 8/4405* (2013.01); *A61B 8/4472* (2013.01); *A61B 8/466* (2013.01); *G01S 7/52073* (2013.01)

(58) Field of Classification Search
CPC ..... A61B 8/085; A61B 8/4472; A61B 8/4405; A61B 8/12; G16H 40/63; G01S 7/52073
See application file for complete search history.

(56) References Cited

U.S. PATENT DOCUMENTS

| | | | | |
|---|---|---|---|---|
| 6,346,940 | B1* | 2/2002 | Fukunaga | G06T 15/20 345/420 |
| 2003/0212327 | A1* | 11/2003 | Wang | A61B 8/466 600/437 |
| 2008/0221446 | A1* | 9/2008 | Washburn | A61B 8/00 600/437 |
| 2010/0030079 | A1* | 2/2010 | Hamada | A61B 8/14 600/443 |
| 2010/0188398 | A1 | 7/2010 | Vion et al. | |
| 2010/0292574 | A1 | 11/2010 | Hyun et al. | |
| 2013/0102903 | A1* | 4/2013 | Tanaka | A61B 8/08 600/447 |
| 2013/0211243 | A1* | 8/2013 | Zhang | A61B 8/463 600/424 |
| 2014/0152656 | A1 | 6/2014 | Yoo et al. | |
| 2014/0228687 | A1* | 8/2014 | Park | A61B 8/085 600/449 |

FOREIGN PATENT DOCUMENTS

| | | |
|---|---|---|
| JP | 2003260052 A | 9/2003 |
| JP | 2009-056239 A | 3/2009 |
| JP | 2012-200403 A | 10/2012 |
| JP | 2014-124269 A | 7/2014 |

\* cited by examiner

ULTRASOUND DIAGNOSIS APPARATUS AND METHOD OF OPERATING THE SAME

RELATED APPLICATION

This application claims the benefit of Korean Patent Application No. 10-2014-0195374, filed on Dec. 31, 2014, in the Korean Intellectual Property Office, the disclosure of which is incorporated herein in its entirety by reference.

BACKGROUND

1. Field

One or more exemplary embodiments relate to an ultrasound diagnosis apparatus and a method of operating the same, and more particularly, to an ultrasound diagnosis apparatus and a method of operating the same, which display positions of objects which are not marked on an ultrasound image.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissues or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound diagnosis apparatuses are widely used together with other image diagnosis apparatuses including a computed tomography (CT) apparatus, a magnetic resonance imaging (MRI) apparatus, and the like.

Ultrasound diagnosis apparatuses may provide a brightness (B) mode in which a reflection coefficient of an ultrasound signal reflected from an object is shown as a two-dimensional (2D) image, a Doppler mode image in which an image of a moving object (particularly, blood flow) is shown by using the Doppler effect, and an elastic mode image in which a reaction difference between when compression is applied to an object and when compression is not applied to the object is expressed as an image.

SUMMARY

One or more exemplary embodiments include an ultrasound diagnosis apparatus and a method of operating the same, which marks a marker for an object, which is not included in an ultrasound image displayed by a display, to correspond to a position of the object.

Additional aspects will be set forth in part in the description which follows and, in part, will be apparent from the description, or may be learned by practice of the presented exemplary embodiments.

According to one or more exemplary embodiments, an ultrasound diagnosis apparatus includes: a data acquirer that acquires ultrasound data about an object; an image processor that generates an ultrasound image, based on the ultrasound data and generates a first marker for a first object of interest (OOI) which is not included in the generated ultrasound image; and a display that displays the generated ultrasound image and marks the first marker to correspond to a position of the first OOI.

The ultrasound data may be three-dimensional (3D) volume data, and the ultrasound image may be a 3D ultrasound image which is generated by volume-rendering the 3D volume data.

The marker may include at least one selected from a text, an image, and a moving image which represent a corresponding OOI.

The image processor may determine a color or a size of the first marker, based on a position of the first OOI.

The image processor may determine a size of the first marker, based on a distance between a region corresponding to the ultrasound image and a point in which the first OOI is located.

The image processor may generate a second marker corresponding to a second OOI which is included in the generated ultrasound image, and the display may mark the second marker on the ultrasound image for the second marker to correspond to a position of the second OOI.

The image processor may differently form at least one selected from colors and sizes of the first marker and the second marker.

When the first OOI is located in a front region of a region corresponding to the ultrasound image with respect to a viewing direction, the display may mark the first marker on the ultrasound image.

The display may mark the first marker on a border region of the ultrasound image when the first OOI is located in at least one selected from a left region, a right region, an upper region, and a lower region of a region corresponding to the ultrasound image with respect to a viewing direction.

The display may mark the first marker on a map image representing a position of a region corresponding to the ultrasound image and a position of the first OOI.

According to one or more exemplary embodiments, a method of operating an ultrasound diagnosis apparatus includes: acquiring ultrasound data about an object; generating an ultrasound image, based on the ultrasound data; generating a first marker for a first object of interest (OOI) which is not included in the generated ultrasound image; and displaying the generated ultrasound image and marking the first marker to correspond to a position of the first OOI.

The ultrasound data may be three-dimensional (3D) volume data, and the ultrasound image may be a 3D ultrasound image which is generated by volume-rendering the 3D volume data.

The marker may include at least one selected from a text, an image, and a moving image which represent a corresponding OOI.

The generating of the first marker may include determining a color or a size of the first marker, based on a position of the first OOI.

The generating of the first marker may include determining a size of the first marker, based on a distance between a region corresponding to the ultrasound image and a point in which the first OOI is located.

The method may further include: generating a second marker corresponding to a second OOI which is included in the generated ultrasound image, and marking the second marker on the ultrasound image for the second marker to correspond to a position of the second OOI.

The method may further include differently forming at least one selected from colors and sizes of the first marker and the second marker.

The marking of the first marker may include marking the first marker on the ultrasound image when the first OOI is located in a front region of a region corresponding to the ultrasound image with respect to a viewing direction.

The marking of the first marker may include marking the first marker on a border region of the ultrasound image when the first OOI is located in at least one selected from a left region, a right region, an upper region, and a lower region of a region corresponding to the ultrasound image with respect to a viewing direction.

The marking of the first marker may include marking the first marker on a map image representing a position of a region corresponding to the ultrasound image and a position of the first OOI.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
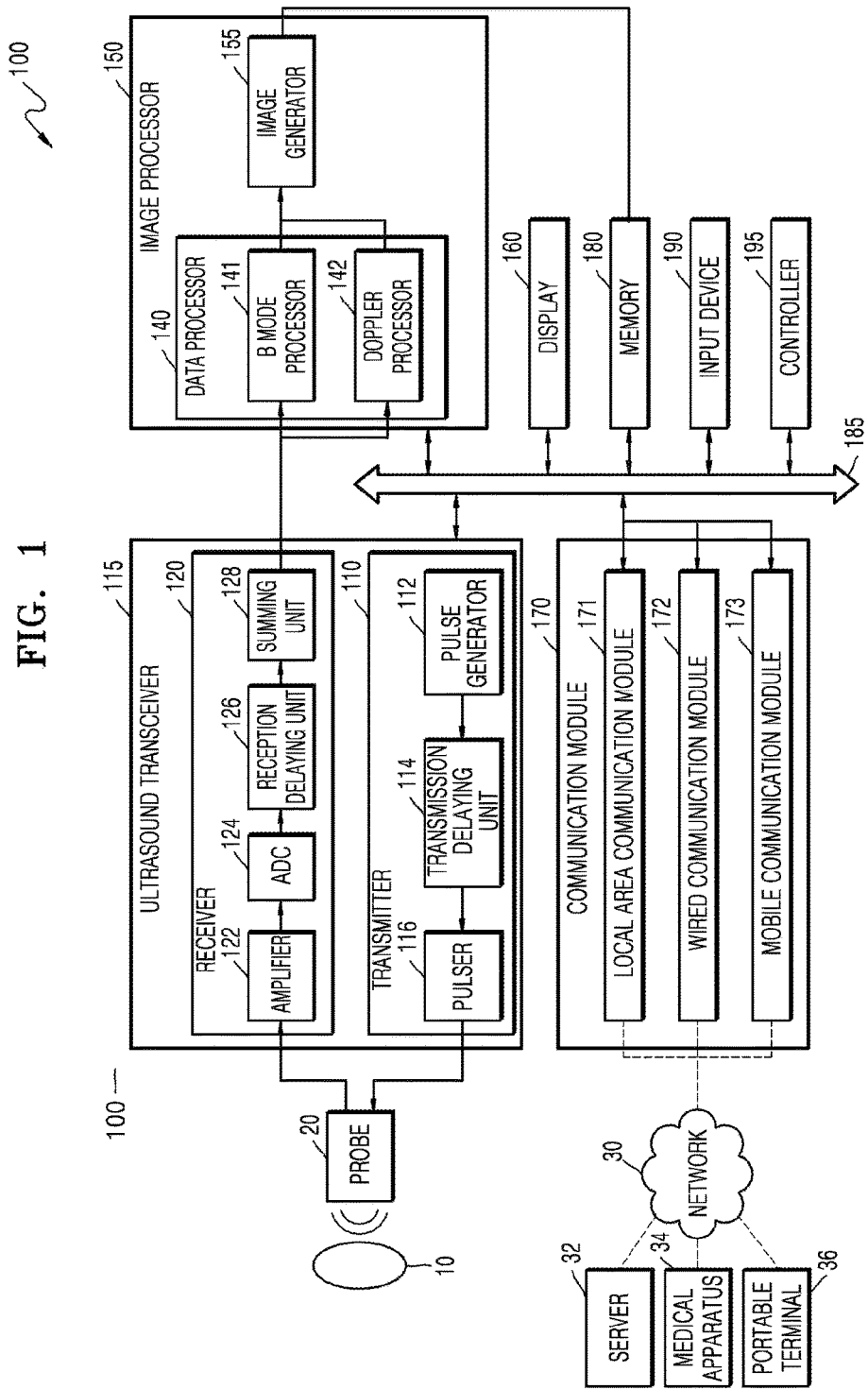
FIG. 1 is a block diagram showing a configuration of an ultrasound diagnosis apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the invention. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Moreover, the ultrasound image may be implemented in various ways. For example, the ultrasound image may be at least one of an amplitude (A) mode image, a brightness (B) mode image, a color (C) mode image, and a Doppler (D) mode image. Also, according to an embodiment of the present invention, the ultrasound image may be a two-dimensional (2D) image or a three-dimensional (3D) image.

Throughout the specification, a "user" may be, but is not limited to, a medical expert, for example, a medical doctor, a nurse, a medical laboratory technologist, or a medical imaging expert, or a technician who repairs medical apparatuses.

Reference will now be made in detail to embodiments, examples of which are illustrated in the accompanying drawings. In this regard, the present embodiments may have different forms and should not be construed as being limited to the descriptions set forth herein.

FIG. 1 is a block diagram showing a configuration of an ultrasound diagnosis apparatus 100 according to an embodiment. Referring to FIG. 1, the ultrasound diagnosis apparatus 100 may include a probe 20, an ultrasound transceiver 115, an image processor 150, a communication module 170, a display 160, a memory 180, an input device 190, and a controller 195, which may be connected to one another via buses 185.

In some embodiments, the ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 115 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 100 by wire or wirelessly, and according to embodiments, the ultrasound diagnosis apparatus 100 may include a plurality of probes 20.

A transmitter 110 supplies a driving signal to the probe 20. The transmitter 110 includes a pulse generator 112, a transmission delaying unit 114, and a pulser 116. The pulse generator 112 generates pulses for forming transmission ultrasound waves based on a predetermined pulse repetition frequency (PRF), and the transmission delaying unit 114 delays the pulses by delay times necessary for determining transmission directionality. The pulses which have been delayed correspond to a plurality of piezoelectric vibrators included in the probe 20, respectively. The pulser 116 applies a driving signal (or a driving pulse) to the probe 20 based on timing corresponding to each of the pulses which have been delayed.

A receiver 120 generates ultrasound data by processing echo signals received from the probe 20. The receiver 120 may include an amplifier 122, an analog-to-digital converter (ADC) 124, a reception delaying unit 126, and a summing unit 128. The amplifier 122 amplifies echo signals in each channel, and the ADC 124 performs analog-to-digital conversion with respect to the amplified echo signals. The reception delaying unit 126 delays digital echo signals output by the ADC 124 by delay times necessary for determining reception directionality, and the summing unit 128 generates ultrasound data by summing the echo signals processed by the reception delaying unit 126. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 150 generates an ultrasound image by scan-converting ultrasound data generated by the ultrasound transceiver 115 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood, a tissue Doppler image showing a movement of tissue, or a spectral Doppler image showing a moving speed of an object as a waveform.

A B mode processor 141 extracts B mode components from ultrasound data and processes the B mode components. An image generator 155 may generate an ultrasound image indicating signal intensities as brightness based on the extracted B mode components 141.

Similarly, a Doppler processor 142 may extract Doppler components from ultrasound data, and the image generator 155 may generate a Doppler image indicating a movement of an object as colors or waveforms based on the extracted Doppler components.

According to an embodiment, the image generator 155 may generate a three-dimensional (3D) ultrasound image via volume-rendering with respect to volume data and may also generate an elasticity image by imaging deformation of the object 10 due to pressure.

Furthermore, the image generator 155 may display various pieces of additional information in an ultrasound image by using text and graphics. In addition, the generated ultrasound image may be stored in the memory 180.

The image processor 150 according to an exemplary embodiment may detect objects of interest (OOIs) included in an object and calculate positions of the detected OOIs, based on ultrasound data about the object. For example, the OOIs may include an organ, a poly, a lump, etc.

The image processor 150 according to an exemplary embodiment may generate a marker corresponding to each of the detected OOIs and determine an attribute of the marker, based on the position of a corresponding OOI. For example, the image processor 150 may determine a size or a color of the marker, based on whether the corresponding OOI is included in the ultrasound image and a distance between a region corresponding to the ultrasound image and a point where the corresponding OOI is positioned.

The display 160 displays the generated ultrasound image. The display 160 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 160 according to exemplary embodiments.

The display 160 may include at least one of a liquid crystal display (LCD), a thin film transistor-liquid crystal display (TFT-LCD), an organic light-emitting diode (OLED), a flexible display, a 3D display, an electrophoretic display, and a transparent display.

Moreover, when the display 160 forms a layer structure along with a user input unit and thus is configured with a touch screen, the display 160 may be used as an input device which enables information to be input by a user's touch, in addition to an output unit.

The touch screen may detect a touch pressure as well as a touch input position and a touched area. Also, the touch screen may detect a proximity touch as well as a real touch.

The display 160 according to an exemplary embodiment may display the ultrasound image. Also, the display 160 may mark the marker generated by the image processor 150 to correspond to the position of the corresponding OOI.

The communication module 170 is connected to a network 30 by wire or wirelessly to communicate with an external device or a server. The communication module 170 may exchange data with a hospital server or another medical apparatus in a hospital, which is connected thereto via a PACS. Furthermore, the communication module 170 may perform data communication according to the digital imaging and communications in medicine (DICOM) standard.

The communication module 170 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 170 may receive information about a diagnosis history or medical treatment schedule of a patient from a server and utilizes the received information to diagnose the patient. Furthermore, the communication module 170 may perform data communication not only with a server or a medical apparatus in a hospital, but also with a portable terminal of a medical doctor or patient.

The communication module 170 is connected to the network 30 by wire or wirelessly to exchange data with a server 32, a medical apparatus 34, or a portable terminal 36. The communication module 170 may include one or more components for communication with external devices. For example, the communication module 1300 may include a local area communication module 171, a wired communication module 172, and a mobile communication module 173.

The local area communication module 171 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 172 refers to a module for communication using electric signals or optical signals. Examples of wired communication techniques according to an embodiment may include communication via a twisted pair cable, a coaxial cable, an optical fiber cable, and an Ethernet cable.

The mobile communication module 173 transmits or receives wireless signals to or from at least one selected from a base station, an external terminal, and a server on a mobile communication network. The wireless signals may be voice call signals, video call signals, or various types of data for transmission and reception of text/multimedia messages.

The memory 180 stores various data processed by the ultrasound diagnosis apparatus 100. For example, the memory 180 may store medical data related to diagnosis of an object, such as ultrasound data and an ultrasound image that are input or output, and may also store algorithms or programs which are to be executed in the ultrasound diagnosis apparatus 100.

The memory 180 may be any of various storage media, e.g., a flash memory, a hard disk drive, EEPROM, etc. Furthermore, the ultrasound diagnosis apparatus 100 may utilize web storage or a cloud server that performs the storage function of the memory 180 online.

The input device 190 refers to a means via which a user inputs data for controlling the ultrasound diagnosis apparatus 50. The input device 190 may include hardware components, such as a keypad, a mouse, a touch pad, a track ball, and a jog switch. However, embodiments are not limited thereto, and the input device 190 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc. Particularly, the input device 190 may include the touch screen which forms the layer structure along with the display 160.

In this case, the ultrasound diagnosis apparatus 100 according to an exemplary embodiment may display an ultrasound image having a certain mode and a control panel for the ultrasound image. Also, the ultrasound diagnosis apparatus 100 may sense through the touch screen a user's touch gesture for the ultrasound image.

The ultrasound diagnosis apparatus 100 according to an exemplary embodiment may physically include some buttons, which are frequently used by a user, among a plurality of buttons included in a control panel of a general ultrasound apparatus, and the other buttons may be provided through the touch screen in a GUI type.

The controller 195 may control all operations of the ultrasound diagnosis apparatus 100. In other words, the controller 195 may control operations among the probe 20, the ultrasound transceiver 100, the image processor 150, the communication module 170, the memory 180, and the user device 190 shown in FIG. 2.

All or some of the probe 20, the ultrasound transceiver 115, the image processor 150, the display 160, the communication module 170, the memory 180, the user device 190, and the controller 195 may be implemented as software modules. However, embodiments of the present invention are not limited thereto, and some of the components stated above may be implemented as hardware modules. Furthermore, at least one selected from the ultrasound transceiver 115, the image processor 150, and the communication module 170 may be included in the controller 195. However, embodiments of the present invention are not limited thereto.

Figure 2:
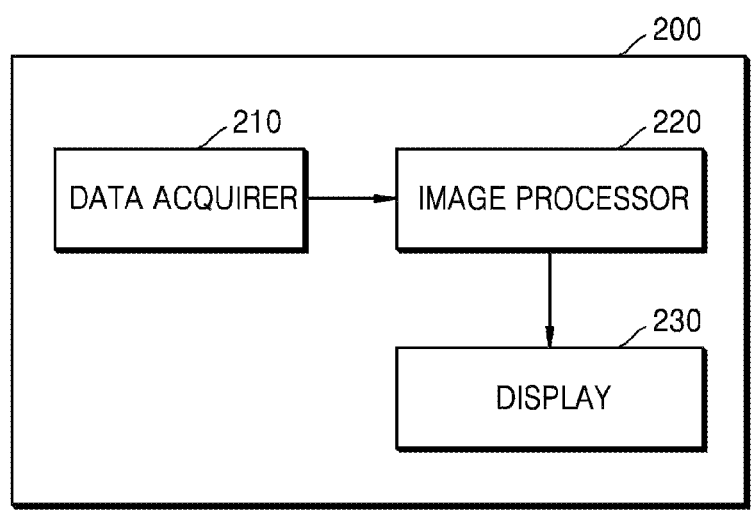
FIG. 2 is a block diagram showing a configuration of an ultrasound diagnosis apparatus according to an exemplary embodiment.

FIG. 2 is a block diagram showing a configuration of an ultrasound diagnosis apparatus 200 according to an exemplary embodiment. Referring to FIG. 2, the ultrasound diagnosis apparatus 200 may include a data acquirer 210, an image processor 220, and a display 230.

The data acquirer 210 of FIG. 2 may be an element corresponding to the probe 20 or ultrasound transceiver 115 of FIG. 1, the image processor 220 of FIG. 2 may be an element corresponding to the image processor 150 of FIG. 1, and the display 240 of FIG. 2 may be an element corresponding to the display 160 of FIG. 1.

The data acquirer 210 may acquire ultrasound data about an object. The data acquirer 210 may transmit an ultrasound wave to the object, and receive an echo signal reflected from the object, thereby 3D volume data.

Alternatively, the data acquirer 210 may receive the 3D volume data from an external device through the communication module 170 of FIG. 1.

The 3D volume data may be data which is acquired by using a phased probe, a linear probe, or a convex probe. A shape of volume data may be changed depending on the kind of a probe.

The image processor 220 may generate an ultrasound image of the object, based on the acquired ultrasound data. In this case, the ultrasound image may be a 2D ultrasound image or a 3D ultrasound image.

For example, the image processor 220 may volume-render the 3D volume data to generate a 3D ultrasound image. Volume-rendering of the 3D ultrasound image may be performed based on a model including volume data, a viewing point, a viewing direction, and a screen.

Figure 3:
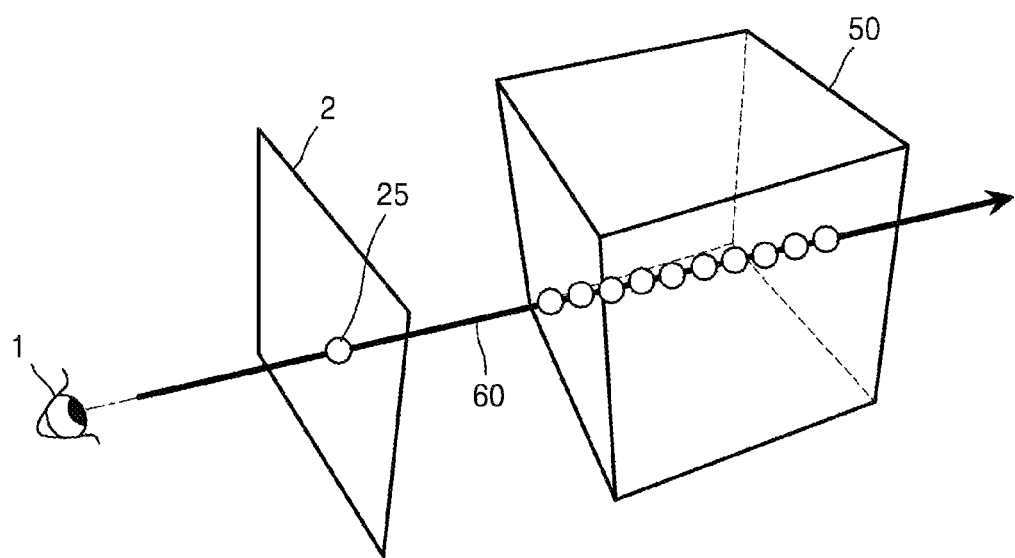
FIG. 3 is a diagram illustrating a method of rendering a three-dimensional (3D) ultrasound image, according to an exemplary embodiment.

Referring to FIG. 3, by volume-rendering the 3D ultrasound image, a viewing point 1 may be determined, and a screen 2 may be determined based on the determined viewing point 1. In this case, the viewing point 1 represents a direction in which a viewer observes 3D volume data 50. Also, the screen 2 represents a projection surface on which the volume data 50 is projected from the viewing point 1, and represents a 2D screen on which an image generated through the volume-rendering is displayed.

The volume data 50 may include a plurality of voxels, and a voxel is a compound word of "volume" and "pixel". If a pixel defines one point of a 2D plane, the voxel defines one point of a 3D space. Also, the pixel includes an x coordinate and a y coordinate, and the voxel includes x, y, and z coordinates.

The ultrasound diagnosis apparatus 200 according to an exemplary embodiment may perform a volume-rendering operation by using a ray casting method. For example, as illustrated in FIG. 3, the ray casting method may irradiate a virtual ray 60 on a pixel 25 of a display screen from the viewing point 1 and detect voxels, through which the ray 60 passes, from the voxels of the volume data 50. Also, the ultrasound diagnosis apparatus 200 may determine a brightness value (or transparency) of the pixel 25, based on brightness values of the detected voxels.

For example, the ultrasound diagnosis apparatus 200 may determine, as the brightness value of the pixel 25, a highest brightness value among the brightness values of the detected voxels. Alternatively, the ultrasound diagnosis apparatus 200 may determine, as the brightness value of the pixel 25, a lowest brightness value among the brightness values of the detected voxels. Alternatively, the ultrasound diagnosis apparatus 200 may determine an average value of the brightness values of the detected voxels as the brightness value of the pixel 25. However, the present embodiment is not limited thereto.

Moreover, the ultrasound diagnosis apparatus 200 may volume-render the volume data 50 by using one of well-known volume-rendering methods in addition to the above-described volume-rendering method.

Moreover, the image processor 220 according to an exemplary embodiment may detect OOIs included in the object and calculate positions of the detected OOIs, based on the ultrasound data about the object. For example, the OOIs may include an organ, a poly, a lump, etc. Also, the OOIs detected and the positions of the OOIs calculated by the image processor 150 may be mapped and stored in the memory 180 of FIG. 1.

The OOIs may be classified into a first OOI, which is not included in the generated ultrasound image, and a second OOI which is included in the generated ultrasound image. For example, in a case of generating a 3D ultrasound image through volume-rendering of volume data, only an OOI located in a region that a virtual ray reaches may be included in an ultrasound image.

On the other hand, an OOI which is not located in the region that the virtual ray reaches may not be included in the ultrasound image. Also, when an OOI is located in the region (a visible region) that the virtual ray reaches, but is covered by another object (when opacity of voxels corresponding to the other object is high), the OOI may not be included in the ultrasound image.

Moreover, the image processor 220 may generate a marker corresponding to each of the detected OOIs. The marker may include at least one selected from a text, an image, and a moving image which represent a corresponding OOI. For example, the marker may be expressed as a text representing a name of the corresponding OOI, and may be expressed as an image or a moving image which corresponds to the corresponding OOI.

The image processor 220 according to an exemplary embodiment may determine a color or a size of a first marker corresponding to the first OOI, based on a position of the first OOI. For example, as a distance between a region corresponding to the ultrasound image and a point where the first OOI is located increases, the image processor 220 may generate the first marker having a relatively smaller size, and as the distance between the region corresponding to the ultrasound image and the point where the first OOI is located decreases, the image processor 220 may generate the first marker having a relatively larger size.

The image processor 220 according to an exemplary embodiment may differently form at least one selected from colors and sizes of the first marker and a second marker corresponding to the second OOI.

The display 230 may display the ultrasound image generated by the image processor 220. For example, illustrated in FIG. 4, an ultrasound image 310 displayed by the display 230 may be a 3D ultrasound image which is generated by volume-rendering volume data. Also, the ultrasound image 310 may be a virtual endoscope image. The virtual endoscope image denotes an image having the same view as that of an image which is obtained by directly photographing the inside of an object with an endoscope inserted into the object.

Figure 4:
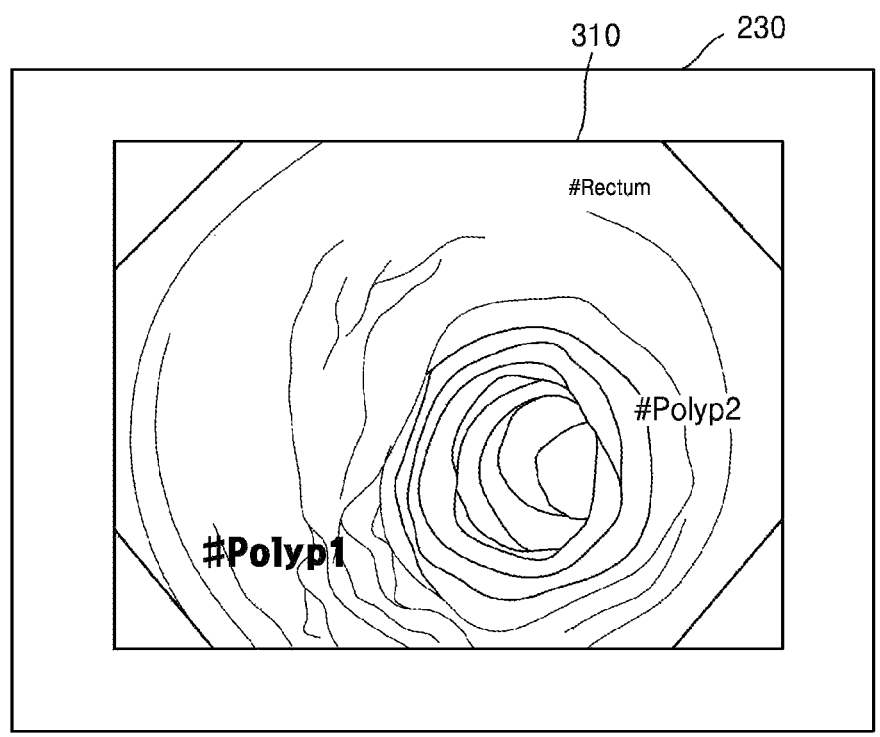
FIG. 4 is a diagram illustrating a 3D ultrasound image according to an exemplary embodiment.

Moreover, as illustrated in FIG. 4, the display 230 may mark the markers (for example, #Polyp1, #Polyp2, and #Rectum) generated by the image processor 220 to correspond to respective positions of the OOIs. In this case, a second marker #Polyp1 corresponding to a second OOI (for example, a polyp) included in the ultrasound image 310 and first markers (for example, #Polyp2 and #Rectum) respectively corresponding to first OOIs (for example, a lump and a rectum) which are not included in the ultrasound image 310 may be marked in different colors. Also, sizes of the first markers (for example, #Polyp2 and #Rectum) may be differently marked based on a distance between points where the first markers are located. For example, a marker #Rectum, which corresponds to the rectum farthest away from a region corresponding to the ultrasound image 310, among the first markers (for example, #Polyp2 and #Rectum) may be smallest marked, and a marker #Polyp2 corresponding to the lump closest to the region corresponding to the ultrasound image 310 may be largest marked.

Moreover, the display 230 may mark the first markers on the ultrasound image 310 when the first OOIs are located in a front region of the region corresponding to the ultrasound image 310 with respect to a viewing direction. Also, the display 230 may mark the first markers on a border region of the ultrasound image 310 when the first OOIs are located in at least one selected from a left region, a right region, an upper region, and a lower region of the region corresponding to the ultrasound image 310 with respect to the viewing direction.

Moreover, the display 230 may mark the second marker on the ultrasound image 310 to correspond to a position of the second OOI.

Moreover, the display 230 may further display a map image that represents a position of the region corresponding to the ultrasound image 310 and positions of the first OOIs.

FIGS. 5 to 8 are diagrams illustrating examples where a marker according to an exemplary embodiment is displayed by a display.

Figure 5A:
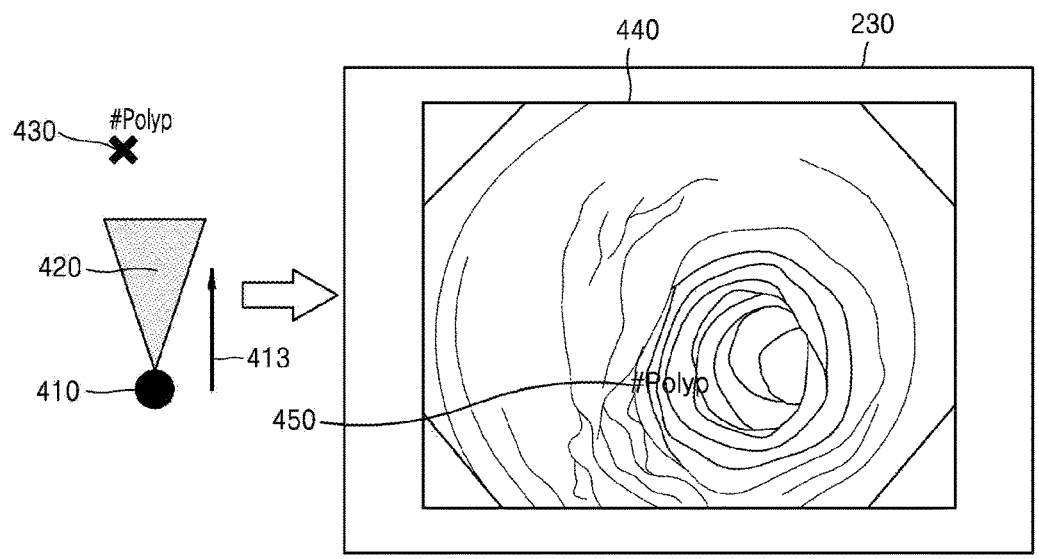
FIGS. 5A to 8B are diagrams illustrating examples where a marker according to an exemplary embodiment is displayed by a display.
Figure 5B:
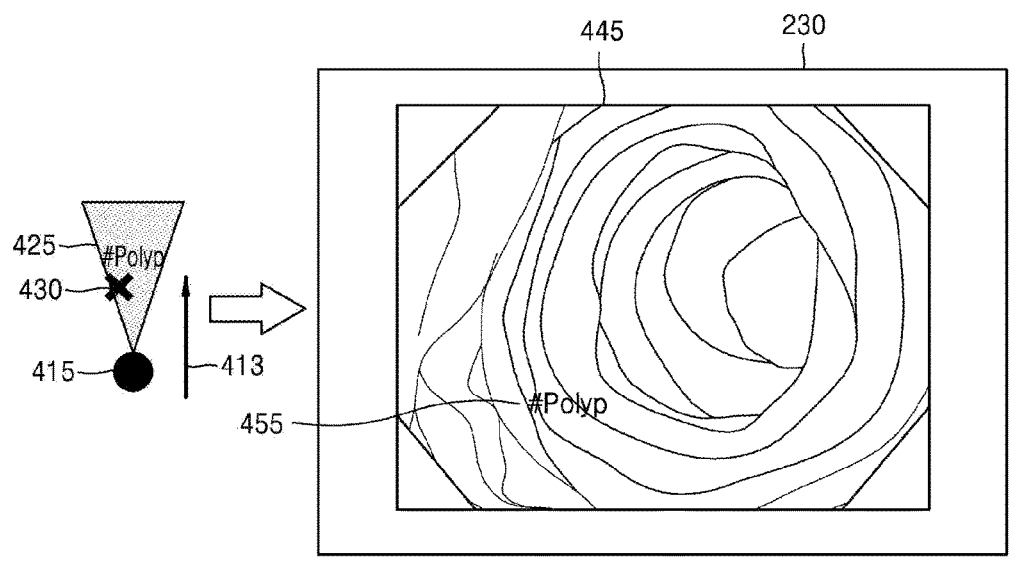

FIG. 5A is a diagram illustrating a case where an OOI according to an exemplary embodiment is not included in an ultrasound image, namely, an example where a marker for a first OOI is marked. FIG. 5B is a diagram illustrating a case where an OOI according to an exemplary embodiment is included in an ultrasound image, namely, an example where a marker for a second OOI is marked.

Referring to FIG. 5A, the display 230 according to an exemplary embodiment may display a rendered 3D ultrasound image (a first ultrasound image 440). The first ultrasound image 440 may be an image which is obtained through rendering based on brightness values of voxels intersecting a virtual ray which is irradiated on 3D volume data in a first viewing direction 413 with a first point 410 as a viewing point.

A first region 420 may be a region which an irradiated virtual ray reaches in volume-rendering a first ultrasound image. Therefore, an OOI (a second OOI) located in the first region 420 may be included in the first ultrasound image 440, but an OOI (a first OOI) which is not located in the first region 420 may not be included in the first ultrasound image 440. For example, as illustrated in FIG. 5A, a virtual ray does not reach a polyp 430 which is not located in the first region 420, and thus, the polyp 430 is not marked on the first ultrasound image 440.

The ultrasound diagnosis apparatus 100 (200) may detect the polyp 430 which is the first OOI, based on ultrasound data about an object and calculate a position of the polyp 430. Also, the ultrasound diagnosis apparatus 100 (200) may generate a first marker (#Polyp) 450 corresponding to the polyp 430, and mark the first marker 450 to correspond to the calculated position of the polyp 430.

For example, as illustrated in FIG. 5A, when the polyp 430 is located in front of the first region 420 along the first viewing direction 413, the ultrasound diagnosis apparatus 100 (200) may mark the first marker (#Polyp) 450 on the first ultrasound image 440. In this case, the ultrasound diagnosis apparatus 100 (200) may mark the first marker (#Polyp) 450, based on a direction of a point where the polyp 430 is located with respect to the first point 410. For example, when the polyp 430 is located at a lower portion of a front left side with respect to the first point 410, as illustrated in FIG. 5A, the first marker (#Polyp) 450 may be marked at a lower portion of a left side with respect to a center of the ultrasound image 440.

A size of the marked first marker (#Polyp) 450 may be determined based on a distance between the first point 410 and a point where the polyp 430 is located. For example, as a distance between the first point 410 and the polyp 430 increases, the ultrasound diagnosis apparatus 100 (200) may small mark the size of the first marker (#Polyp) 450. Therefore, when the first marker (#Polyp) 450 is small marked, a user easily recognizes that the polyp 430 is far away from the first point 410.

Referring to FIG. 5B, the ultrasound diagnosis apparatus 100 (200) may move a viewing point from the first point 410 to a second point 415 without changing the viewing direction 413, and render the ultrasound data, thereby generating a second ultrasound image 445.

When the viewing point is moved from the first point 410 to the second point 415, the region which the virtual ray reaches may be moved from the first region 420 to a second region 425. Therefore, the polyp 430 may be located in the second region 425 and may be included in the second ultrasound image 445.

The ultrasound diagnosis apparatus 100 (200) may generate a second marker (#Polyp) 455 corresponding to a polyp 425 which is a second OOI, and mark the second marker (#Polyp) 455 on a region where the polyp 425 is located in the second ultrasound image 445.

Moreover, a size of the marked second marker (#Polyp) 455 may be determined based on a distance between the second point 415 and a point where the polyp 425 is located. For example, as a distance between the second point 415 and the polyp 425 increases, the ultrasound diagnosis apparatus 100 (200) may small mark the size of the second marker (#Polyp) 455, and as the distance between the second point 415 and the polyp 425 decreases, the ultrasound diagnosis apparatus 100 (200) may largely mark the size of the second marker (#Polyp) 455. Therefore, when the second marker (#Polyp) 455 is small marked, a user easily recognizes that the polyp 425 is far away from the second point 415.

Moreover, the ultrasound diagnosis apparatus 100 (200) may mark a second marker, corresponding to a second OOI included in an ultrasound image, in a color different from that of a first marker corresponding to a first OOI which is not included in the ultrasound image. For example, the first marker (#Polyp) 450 illustrated in FIG. 5A may be marked in a first color, and the second marker (#Polyp) 455 illustrated in FIG. 5B may be marked in a second color.

Accordingly, the user easily determines whether an OOI corresponding to a marker is included in an ultrasound image.

Figure 6A:
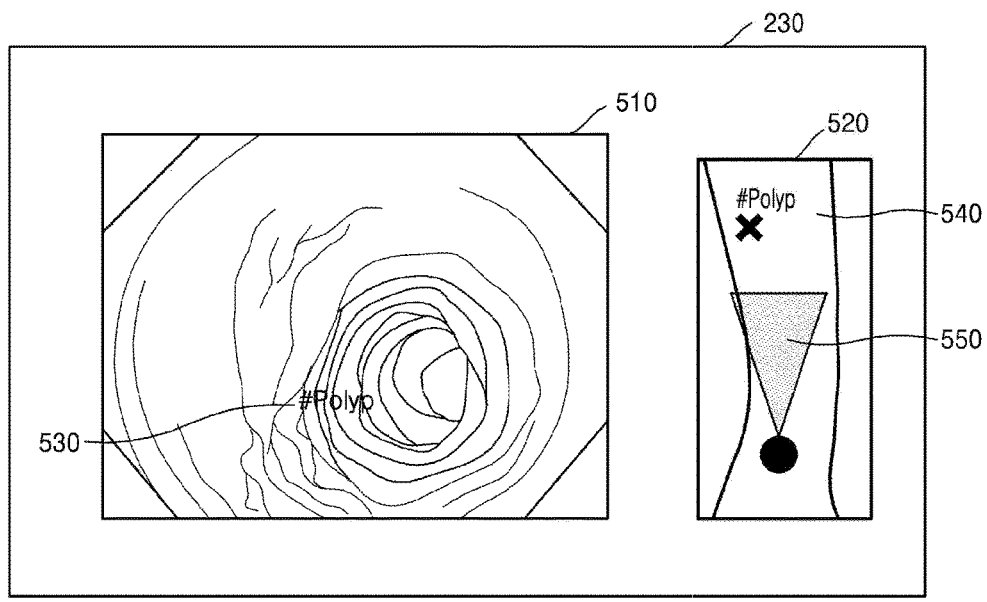
Figure 6B:
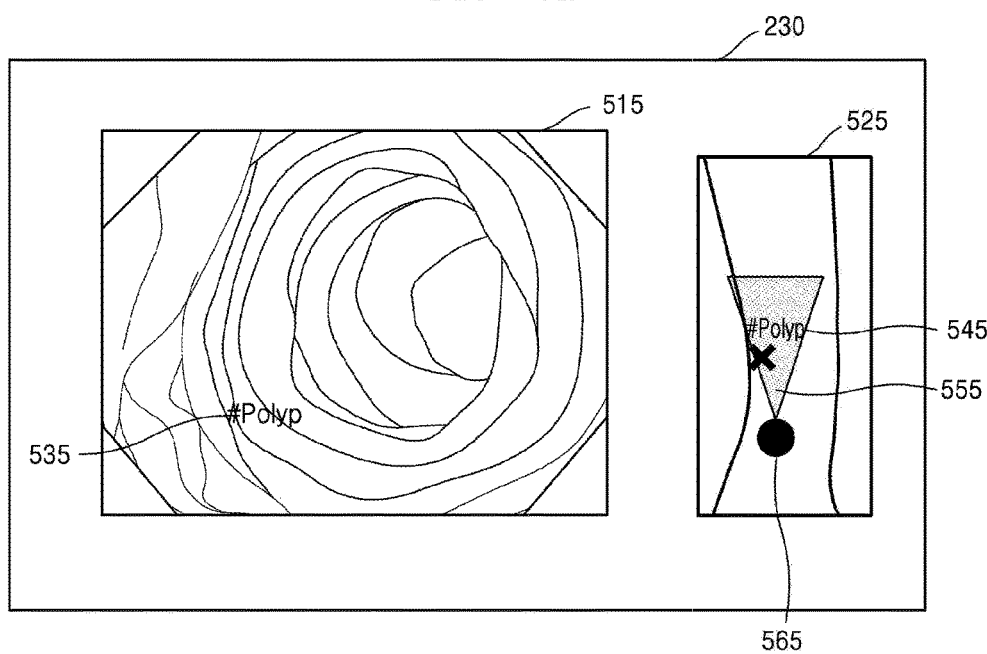

Referring to FIGS. 6A and 6B, the ultrasound diagnosis apparatus 100 (200) may display ultrasound images 510 and 515 and map images 520 and 525. A first map image 520 may be an image that represents a viewing point corresponding to a first ultrasound image 510, a viewing direction, a region that a virtual ray reaches, and positions of extracted OOIs. Also, a second map image 525 may be an image that represents a viewing point corresponding to a second ultrasound image 515, a viewing direction, a region that a virtual ray reaches, and positions of extracted OOIs.

Moreover, the map images 520 and 525 may be images where viewing points corresponding to the ultrasound images 510 and 515, a viewing direction, a region that a virtual ray reaches, and positions of extracted OOIs are marked to overlap on a slice image of an object.

Moreover, the ultrasound diagnosis apparatus 100 (200) may mark a marker according to an exemplary embodiment on a map image in order for the mark to correspond to a position of an OOI. For example, referring to FIG. 6A, the ultrasound diagnosis apparatus 100 (200) may mark a first marker (#Polyp) 540, corresponding to an OOI (a first OOI) which is not included in the first ultrasound image 510, on the first map image 520. In this case, the first marker (#Polyp) 540 may be marked at a certain point outside a first region 550 (a region that a virtual ray reaches). Therefore, a user easily recognizes that an OOI corresponding to the first marker (#Polyp) 540 marked outside the first region is not included in an ultrasound image.

Moreover, referring to FIG. 6B, the ultrasound diagnosis apparatus 100 (200) may mark a second marker (#Polyp) 545, corresponding to an OOI (a second OOI) which is included in the second ultrasound image 515, on the second map image 525. In this case, the second marker (#Polyp) 545 may be marked at a certain point inside a second region 555 (a region that a virtual ray reaches). Therefore, the user easily recognizes that an OOI corresponding to the second marker (#Polyp) 545 marked in the second region 555 is included in the ultrasound image.

Moreover, the ultrasound diagnosis apparatus 100 (200) may adjust a viewing point and a viewing direction in order for a certain OOI to be marked on an ultrasound image, based on a viewing point, a viewing direction, a region that a virtual ray reaches, and a position relationship of a first marker.

For example, as marked on the first map image 520 of FIG. 6A, when a polyp is positioned in front of the first region 550, the ultrasound diagnosis apparatus 100 (200) may maintain a viewing direction and move a viewing point to a second point 565, and perform control in order for the polyp to be added into a region 555 that a virtual ray reaches. Therefore, the polyp may be marked on the second ultrasound image 515.

Figure 7A:
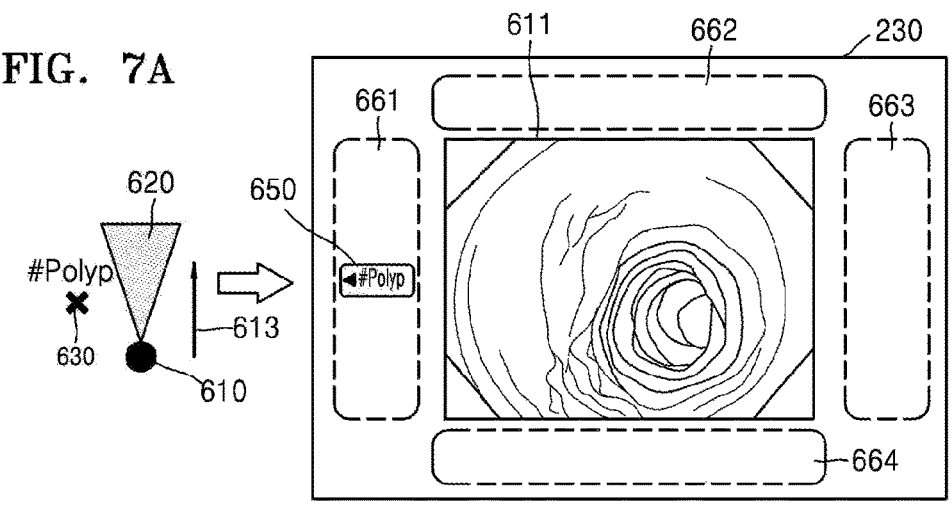
Figure 7B:
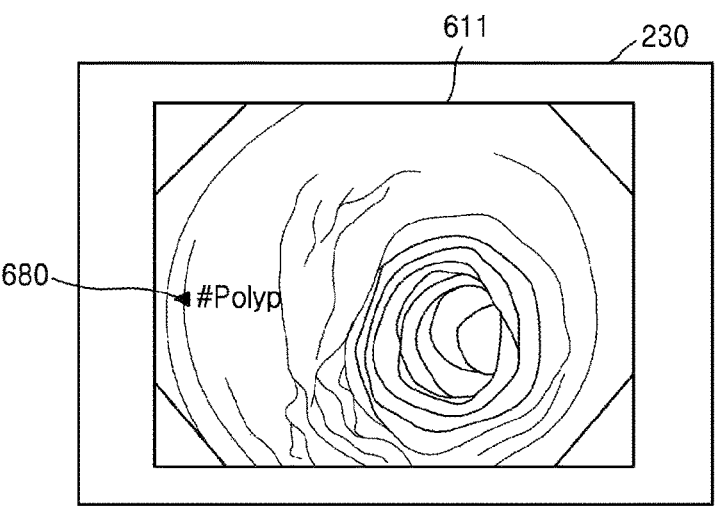
Figure 7C:
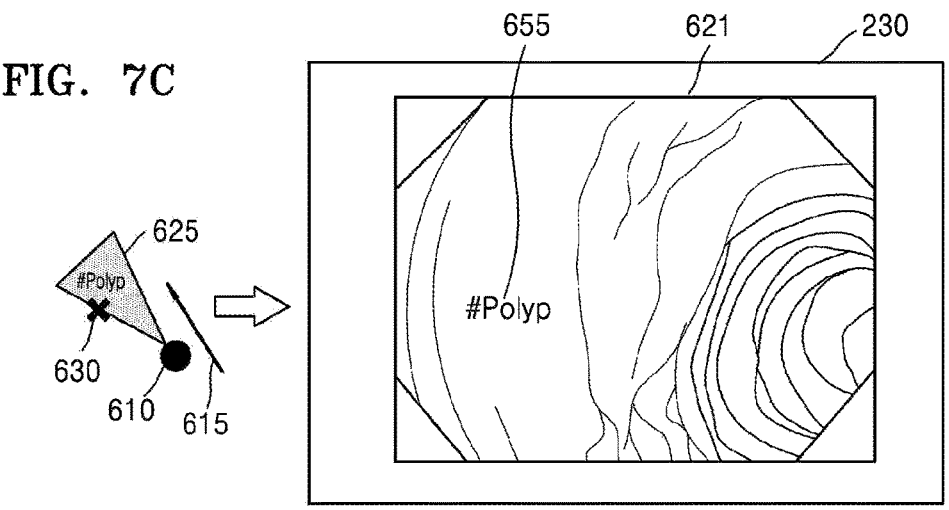

FIGS. 7A and 7B are diagrams illustrating an example where a marker for a first OOI according to an exemplary embodiment is marked, and FIG. 7C is a diagram illustrating an example where a marker for a second OOI according to an exemplary embodiment is marked.

Referring to FIG. 7A, the display 230 according to an exemplary embodiment may display a rendered 3D ultrasound image (a first ultrasound image) 611. The first ultrasound image 611 may be an image which is obtained through rendering based on brightness values of voxels intersecting a virtual ray which is irradiated on 3D volume data in a first viewing direction 613 with a first point 610 as a viewing point.

A first region 620 may be a region which an irradiated virtual ray reaches in volume-rendering the first ultrasound image 611. Therefore, an OOI (a second OOI) located in the first region 620 may be included in the first ultrasound image 611, but an OOI (a first OOI) which is not located in the first region 620 may not be included in the first ultrasound image 440. For example, as illustrated in FIG. 7A, a virtual ray does not reach a polyp 630 which is not located in the first region 620, and thus, the polyp 630 is not marked on the first ultrasound image 611.

The ultrasound diagnosis apparatus 100 (200) may detect the polyp 630 which is the first OOI, based on ultrasound data about an object and calculate a position of the polyp 630. Also, the ultrasound diagnosis apparatus 100 (200) may generate a marker (a first marker) 650 corresponding to the polyp 630, and mark the first marker 650 to correspond to the calculated position of the polyp 630.

For example, as illustrated in FIG. 7A, when the polyp 630 is not located in a first viewing direction 613, the ultrasound diagnosis apparatus 100 (200) may mark the marker 650 on border regions 661 to 664 of the first ultrasound image 611. In this case, the ultrasound diagnosis apparatus 100 (200) may mark the marker 650, based on a direction of a region where the polyp 630 is located with respect to the first region 620. For example, when the polyp 630 is located in a left region of the first region 620 with respect to the first viewing direction 613, the ultrasound diagnosis apparatus 100 (200) may mark the marker 650 on a left region 661 among the border regions 661 to 664 of the first ultrasound image 611.

Moreover, when the polyp 630 is located in a right region of the first region 620, the ultrasound diagnosis apparatus 100 (200) may mark the marker 650 on a right region 663 among the border regions 661 to 664 of the first ultrasound image 611. Also, when the polyp 630 is located in an upper region 662 of the first region 620, the ultrasound diagnosis apparatus 100 (200) may mark the marker 650 on an upper region 662 among the border regions 661 to 664 of the first ultrasound image 611. Also, when the polyp 630 is located in a lower region of the first region 620, the ultrasound diagnosis apparatus 100 (200) may mark the marker 650 on a lower region 614 among the border regions 661 to 664 of the first ultrasound image 611.

Moreover, when the polyp 630 is located higher than a camera with respect to a height of the camera, the ultrasound diagnosis apparatus 100 (200) may mark the marker 650 on an upper end of a left region 661, and when the polyp 630 is located lower than the camera with respect to the height of the camera, the ultrasound diagnosis apparatus 100 (200) may mark the marker 650 on a lower end of the left region 661.

Moreover, a size of the marked marker 650 may be determined based on a distance between the first point 610 and a point where the polyp 630 is located. For example, as a distance between the first point 610 and the polyp 630 increases, the ultrasound diagnosis apparatus 100 (200) may small mark the size of the marker 650. Therefore, when the marker 650 is small marked, the user easily recognizes that the polyp 630 is far away from the first point 610.

Referring to FIG. 7B, the ultrasound diagnosis apparatus 100 (200) may mark a marker 680, corresponding to the polyp 630, on the first ultrasound image 611.

The ultrasound diagnosis apparatus 100 (200) may mark the marker 680, based on a direction of a region where the polyp 630 is located with respect to the first region 620. For example, when the polyp 630 is located in the left region of the first region 620 with respect to the first viewing direction 613, the ultrasound diagnosis apparatus 100 (200) may mark the marker 680 on the left region 661 of the first ultrasound image 611.

Moreover, when the polyp 630 is located in the right region of the first region 620, the ultrasound diagnosis apparatus 100 (200) may mark the marker 680 on a right region of the first ultrasound image 611. Also, when the polyp 630 is located in an upper region of the first region 620, the ultrasound diagnosis apparatus 100 (200) may mark the marker 680 on an upper region of the first ultrasound image 611. Also, when the polyp 630 is located in a lower region of the first region 620, the ultrasound diagnosis apparatus 100 (200) may mark the marker 680 on a lower region of the first ultrasound image 611. Referring to FIG. 7C, the ultrasound diagnosis apparatus 100 (200) may change a viewing direction from the first viewing direction 613 to the second viewing direction 615 without changing the viewing point 610, and render ultrasound data, thereby generating a second ultrasound image 621.

When the viewing direction is moved from the first viewing direction 613 to the second viewing direction 615, a region that a virtual ray reaches may be moved from the first region 620 to the second region 625. Therefore, the polyp 630 may be located in the second region 625, and may be included in the second ultrasound image 621.

Moreover, the ultrasound diagnosis apparatus 100 (200) may generate a second marker (#Polyp) 655 corresponding to the polyp 630 that is a second OOI, and mark the second marker (#Polyp) 655 on a region where the polyp 630 is located in the second ultrasound image 621. In this case, a size of the second marker (#Polyp) 655 may be determined based on a distance between the first point 610 and a point where the polyp 630 is located, and the second marker (#Polyp) 655 may be marked in a color different from that of the first marker 650.

Figure 8A:
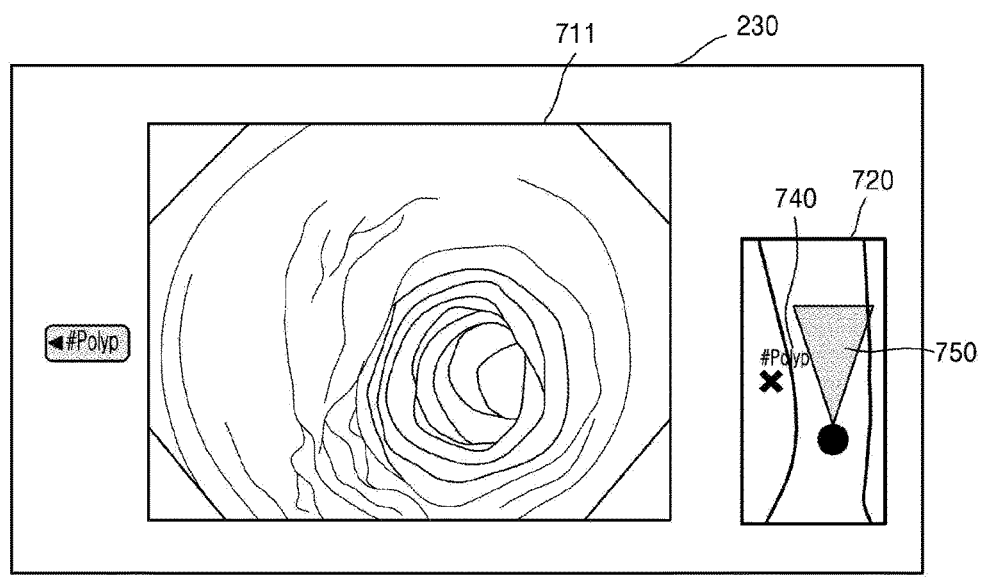
Figure 8B:
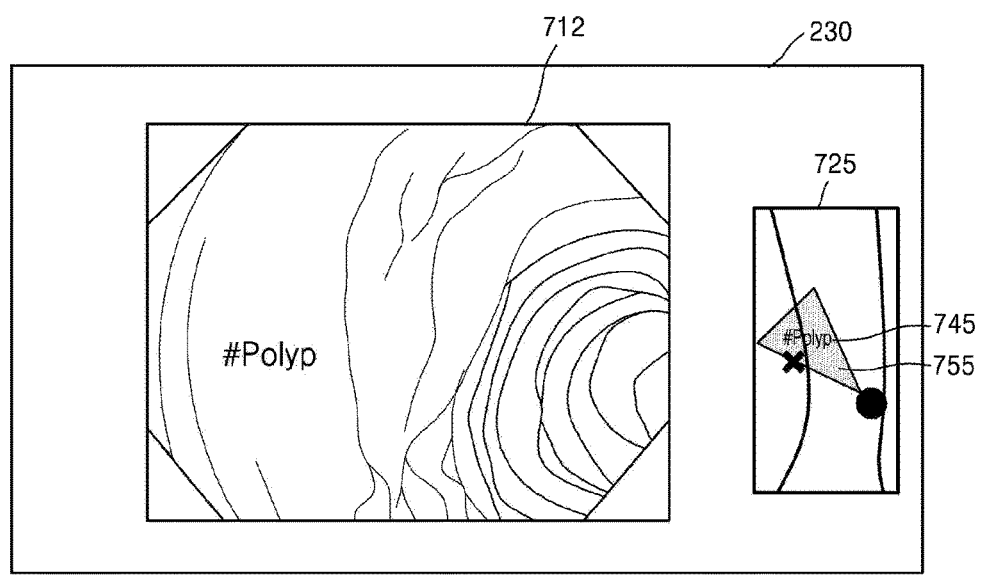

Referring to FIGS. 8A and 8B, the ultrasound diagnosis apparatus 100 (200) may display ultrasound images 711 and 712 and map images 720 and 725. The map images 720 and 725 may be images that represent viewing points corresponding to the ultrasound images 711 and 712, a viewing direction, a region that a virtual ray reaches, and positions of extracted OOIs.

Moreover, the map images 720 and 725 may be images where viewing points corresponding to the ultrasound images 711 and 712, a viewing direction, a region that a virtual ray reaches, and positions of extracted OOIs are marked to overlap on a slice image of an object.

Moreover, the ultrasound diagnosis apparatus 100 (200) may mark a marker according to an exemplary embodiment on a map image in order for the mark to correspond to a position of an OOI. For example, referring to FIG. 8A, the ultrasound diagnosis apparatus 100 (200) may mark a first marker (#Polyp) 740, corresponding to an OOI (a first OOI) which is not included in the first ultrasound image 711, on a first map image 720. In this case, the first marker (#Polyp) 740 may be marked at a certain point outside a first region 750 (a region that a virtual ray reaches). Therefore, the user easily recognizes that an OOI corresponding to the first marker (#Polyp) 740 marked outside the first region 750 is not included in an ultrasound image.

Moreover, referring to FIG. 8B, the ultrasound diagnosis apparatus 100 (200) may mark a second marker (#Polyp) 745, corresponding to an OOI (a second OOI) which is included in the second ultrasound image 712, on the second map image 525. In this case, the second marker (#Polyp) 745 may be marked at a certain point inside a second region 755 (a region that a virtual ray reaches). Therefore, the user easily recognizes that an OOI corresponding to the second marker (#Polyp) 745 marked in the second region is included in the ultrasound image.

Moreover, the ultrasound diagnosis apparatus 100 (200) may adjust a viewing point and a viewing direction in order for a certain OOI to be marked on an ultrasound image, based on a viewing point, a viewing direction, a region that a virtual ray reaches, and a position relationship of a first marker.

For example, as marked on the first map image 720 of FIG. 8A, when a polyp is positioned in a left region of the first region 750, the ultrasound diagnosis apparatus 100 (200) may maintain a viewing direction and move only a viewing point, and perform control in order for the polyp to be added into a region 755 that a virtual ray reaches.

Therefore, the polyp may be marked on the second ultrasound image 712.

Figure 9:
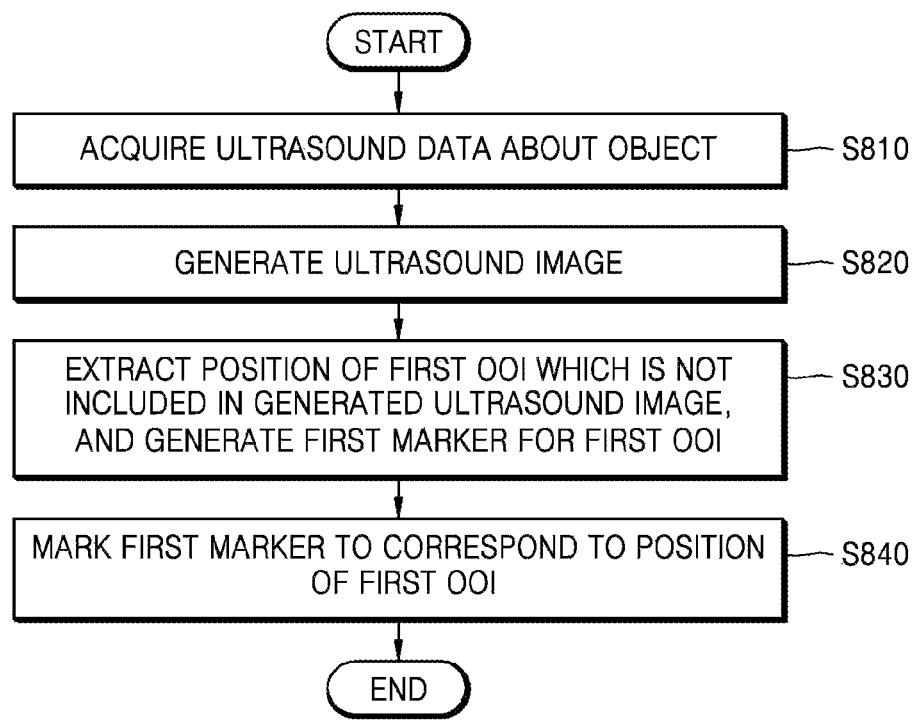
FIG. 9 is a flowchart illustrating a method of operating an ultrasound diagnosis apparatus, according to an exemplary embodiment.

FIG. 9 is a flowchart illustrating a method of operating an ultrasound diagnosis apparatus, according to an exemplary embodiment.

Referring to FIG. 9, in operation S810, the ultrasound diagnosis apparatus 100 (200) may acquire ultrasound data about an object.

The ultrasound diagnosis apparatus 100 (200) may transmit an ultrasound wave to the object, and receive an echo signal reflected from the object, thereby acquiring the ultrasound data. Alternatively, the ultrasound diagnosis apparatus 100 (200) may receive the ultrasound data from an external device. The ultrasound data according to an exemplary embodiment may be 3D volume data.

In operation S820, the ultrasound diagnosis apparatus 100 (200) may generate an ultrasound image, based on the ultrasound data.

The ultrasound diagnosis apparatus 100 (200) may generate a 2D ultrasound image or a 3D ultrasound image. For example, the ultrasound diagnosis apparatus 100 (200) may volume-render the 3D volume data to generate the 3D ultrasound image. Volume-rendering of the 3D ultrasound image may be performed based on a model including volume data, a viewing point, a viewing direction, and a screen.

The ultrasound diagnosis apparatus 100 (200) according to an exemplary embodiment may perform a volume-rendering operation by using the ray casting method. For example, as described above with reference to in FIG. 3, the ray casting method may a rendering technique that irradiates a virtual ray on a pixel of a display screen from a viewing point, detects voxels, through which the ray passes, from voxels of volume data, and determines a brightness value (or transparency) of the pixel, based on brightness values of the detected voxels.

Therefore, an ultrasound image of a region (volume data that a virtual ray reaches) that the virtual ray reaches may be generated.

In operation S830, the ultrasound diagnosis apparatus 100 (200) may extract a position of a first OOI which is not included in the generated ultrasound image, and generate a first marker for the first OOI.

For example, the ultrasound diagnosis apparatus 100 (200) may detect OOIs included in the object and calculate positions of the detected OOIs, based on the ultrasound data about the object. For example, the OOIs may include an organ, a poly, a lump, etc. Also, the ultrasound diagnosis apparatus 100 (200) may map and store the OOIs and the positions of the OOIs.

Moreover, the ultrasound diagnosis apparatus 100 (200) may generate a marker corresponding to each of the detected OOIs. The marker may include at least one selected from a text, an image, and a moving image which represent a corresponding OOI.

The OOIs may be classified into a first OOI, which is not included in the generated ultrasound image, and a second OOI which is included in the generated ultrasound image.

The ultrasound diagnosis apparatus 100 (200) may determine a color or a size of the first marker corresponding to the first OOI, based on a position of the first OOI. For example, as a distance between a region corresponding to the ultrasound image and a point where the first OOI is located increases, the ultrasound diagnosis apparatus 100 (200) may generate the first marker having a relatively smaller size, and as the distance between the region corresponding to the ultrasound image and the point where the first OOI is located decreases, the ultrasound diagnosis apparatus 100 (200) may generate the first marker having a relatively larger size. Also, the ultrasound diagnosis apparatus 100 (200) may differently form at least one selected from colors and sizes of the first marker and a second marker corresponding to the second OOI.

In operation S840, the ultrasound diagnosis apparatus 100 (200) may mark a first marker on a position of the first OOI.

For example, the ultrasound diagnosis apparatus 100 (200) may mark the first marker on the generated ultrasound image. In this case, the ultrasound diagnosis apparatus 100 (200) may mark the first marker with respect to a viewing point corresponding to the generated ultrasound image, based on a direction of a point where an OOI corresponding to the first marker is located.

Moreover, the ultrasound diagnosis apparatus 100 (200) may mark the first marker on one region of an outer region of the ultrasound image with respect to a certain region of the object corresponding to the ultrasound image, based on a direction where an OOI corresponding to the first marker is located.

As described above, according to the one or more of the above exemplary embodiments, a marker for an OOI which is not included in an ultrasound image is marked to correspond to a position of the OOI, thereby enabling the position of the OOI to be easily recognized. Accordingly, scan efficiency and convenience of a user are enhanced.

The ultrasound diagnosis apparatus and the method of operating the same according to embodiments of the present invention may also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage. The computer readable recording medium can also be distributed over network coupled computer systems so that the computer readable code may be stored and executed in a distributed fashion.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:
1. An ultrasound diagnosis apparatus comprising:
an ultrasound probe;
a display;
an image processor; and
a memory storing instructions that, when executed by the image processor, cause the image processor to perform operations comprising:
acquiring ultrasound data about an object representing a part of a human or animal from the ultrasound probe;
generating a first ultrasound image in a first viewing direction with a first viewing point and a map image corresponding to the first ultrasound image, based on the acquired ultrasound data;
detecting objects of interest (OOIs) representing at least one of an organ, a polyp, or a lump in the object, based on the acquired ultrasound data;

determining a first object of interest (OOI) which is not included in the first ultrasound image among the OOIs, based on the first ultrasound image;

controlling the display to display the map image representing a relationship between a first region that a virtual ray reaches based on the first viewing direction with the first viewing point and a position of the first OOI; and controlling the display to display a first marker corresponding to the position of the first OOI outside or inside of the first ultrasound image, based on the relationship between the first region that the virtual ray reaches and the position of the first OOI;

adjusting at least one of the first viewing point or the first viewing direction to be a second viewing point or a second viewing direction, respectively, based on the relationship, so that the position of the first OOI is included in an area that the virtual ray reaches; and controlling the display to display a second ultrasound image based on the at least one of the second viewing point or the second viewing direction, and to display a second marker corresponding to the position of the first OOI on the second ultrasound image, wherein, when the position of the first OOI is not included in the area that the virtual ray reaches, the controlling the display to display the first marker includes:

controlling the display to display the first marker in a border region among outer border regions of the first ultrasound image, based on the relationship.

2. The ultrasound diagnosis apparatus of claim 1, wherein the ultrasound data is three-dimensional (3D) volume data, and each of the first and second ultrasound images is a 3D ultrasound image which is generated by volume-rendering the 3D volume data.

3. The ultrasound diagnosis apparatus of claim 1, wherein the first marker comprises at least one selected from a text, an image, and a moving image which represent the first OOI.

4. The ultrasound diagnosis apparatus of claim 1, wherein the image processor determines a color or a size of the first marker, based on the position of the first OOI.

5. The ultrasound diagnosis apparatus of claim 4, wherein the image processor determines the size of the first marker, based on a distance between the first viewing point and a point indicating the position of the first OOI.

6. The ultrasound diagnosis apparatus of claim 1, wherein, the image processor generates a third marker corresponding to a second OOI which is included in the second ultrasound image, and the display marks the third marker on the second ultrasound image for the third marker corresponding to a position of the second OOI.

7. The ultrasound diagnosis apparatus of claim 6, wherein the display marks the third marker in a color or size different from the first marker.

8. The ultrasound diagnosis apparatus of claim 1, wherein when the first OOI is located in a second region that is in front of a region corresponding to the first ultrasound image with respect to the first viewing direction, the image processor controls the display to mark the first marker on the first ultrasound image.

9. The ultrasound diagnosis apparatus of claim 1, wherein the image processor controls the display to mark the first marker on the border region of the first ultrasound image when the first OOI is located in at least one selected from a left region, a right region, an upper region, and a lower region of a region corresponding to the first ultrasound image with respect to the first viewing direction.

10. A method of operating an ultrasound diagnosis apparatus, the method comprising:

acquiring, by an image processor, ultrasound data about an object representing a part of a human or animal;

generating, by the image processor, a first ultrasound image in a first viewing direction with a first viewing point and a map image corresponding to the first ultrasound image, based on the ultrasound data;

detecting, by the image processor, objects of interest (OOIs) representing at least one of an organ, a polyp, or a lump in the object, based on the acquired ultrasound data;

determining, by the image processor, a first object of interest (OOI) which is not included in the first ultrasound image among the OOIs based on the first ultrasound image;

controlling, by the image processor, a display to display the first map image representing a relationship between a first region that a virtual ray reaches based on the first viewing direction with the first viewing point and a position of the first OOI; and controlling, by the image processor, the display to display a first marker corresponding to the position of the first OOI outside or inside of the first ultrasound image, based on the relationship between the first region that the virtual ray reaches and the position of the first OOI;

adjusting by the image processor, at least one of the first viewing point or the first viewing direction to be a second viewing point or a second viewing direction, respectively, based on the relationship, so that the position of the first OOI is included in an area that the virtual ray reaches; and controlling, by the image processor, the display to display a second ultrasound image based on the at least one of the second viewing point or the second viewing direction, and to display a second marker corresponding to the position of the first OOI on the second ultrasound image, wherein, when the position of the first OOI is not included in the area that the virtual ray reaches, the controlling the display to display the first marker comprises controlling the display to display the first marker in a first border region among outer border regions of the first ultrasound image, based on the relationship.

11. The method of claim 10, wherein the ultrasound data is three-dimensional (3D) volume data, and each of the first and second ultrasound images is a 3D ultrasound image which is generated by volume-rendering the 3D volume data.

12. The method of claim 10, wherein the first marker comprises at least one selected from a text, an image, and a moving image which represent the first OOI.

13. The method of claim 10, wherein the generating of the first marker comprises determining a color or a size of the first marker, based on the position of the first OOI.

14. The method of claim 13, wherein the generating of the first marker comprises determining the size of the first marker, based on a distance between the first viewing point and a point indicating the position of the first OOI.

15. The method of claim 10, further comprising:

generating a third marker corresponding to a second OOI which is included in the second ultrasound image, and marking the third marker on the second ultrasound image for the third marker corresponding to a position of the second OOI.

16. The method of claim 15, wherein the marking the third marker comprises marking the third marker in a color or size different from the first marker.

17. The method of claim 10, wherein the controlling the display to display the first marker comprises marking the first marker on the first ultrasound image when the first OOI is located in a second region that is in front of a region corresponding to the first ultrasound image with respect to the first viewing direction.

18. The method of claim 10, wherein the controlling the display to display the first marker comprises marking the first marker on a border region of the first ultrasound image when the first OOI is located in at least one selected from a left region, a right region, an upper region, and a lower region of a region corresponding to the first ultrasound image with respect to the first viewing direction.

* * * * *